United States Patent [19]

Ascher

[11] Patent Number: 5,355,883
[45] Date of Patent: Oct. 18, 1994

[54] ELECTRODE CONNECTOR, IN PARTICULAR FOR ELECTROCARDIOGRAM ELECTRODES, AND ELECTRODE ASSEMBLY COMPRISING A CONNECTOR OF THIS KIND

[76] Inventor: Gilles Ascher, 36, rue de la Ferme, 92200 Neuilly, France

[21] Appl. No.: 995,993

[22] Filed: Dec. 23, 1992

[30] Foreign Application Priority Data

Dec. 27, 1991 [EP] European Pat. Off. ......... 91403552.2

[51] Int. Cl.$^5$ ............................................. A61B 5/0402
[52] U.S. Cl. .................................... 128/641; 439/488; 439/909; 439/913
[58] Field of Search ...................... 128/639–641, 128/643, 644; 439/488, 489, 577, 620, 909, 913

[56] References Cited

U.S. PATENT DOCUMENTS

| 3,388,590 | 6/1968 | Dryden | 439/489 X |
| 4,308,873 | 1/1982 | Maynard | 128/643 X |
| 4,996,989 | 3/1991 | Stundel et al. | 128/639 |

FOREIGN PATENT DOCUMENTS 1173981  8/1985  U.S.S.R. ............................. 128/639

Primary Examiner—Lee S. Cohen
Attorney, Agent, or Firm—Bachman & Lapointe

[57] ABSTRACT

An electrode connector, for example a connector for electrocardiogram electrodes, has a connection head made from a material that is a good conductor of electricity, a contact member made from a material that is a good conductor of electricity and that is adapted to contact the connection head, a member for snap-fastening the connector to the connection head, an electrically insulative material protective cap at least partially enclosing the contact member and an electric cable comprising at least one electric conductor connected to the contact member. The electrode connector further comprises a device for detecting strain generating artefacts and comprising a strain sensor accommodated in the cap between at least part of the contact member and at least one interior area of the cap. At least one other electric conductor is connected to said strain sensor.

9 Claims, 1 Drawing Sheet

FIG_1
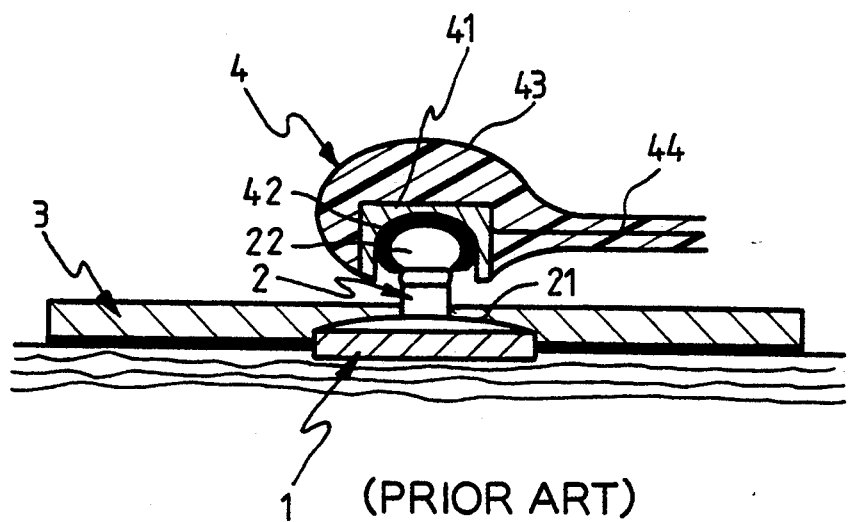
(PRIOR ART)
FIG_2
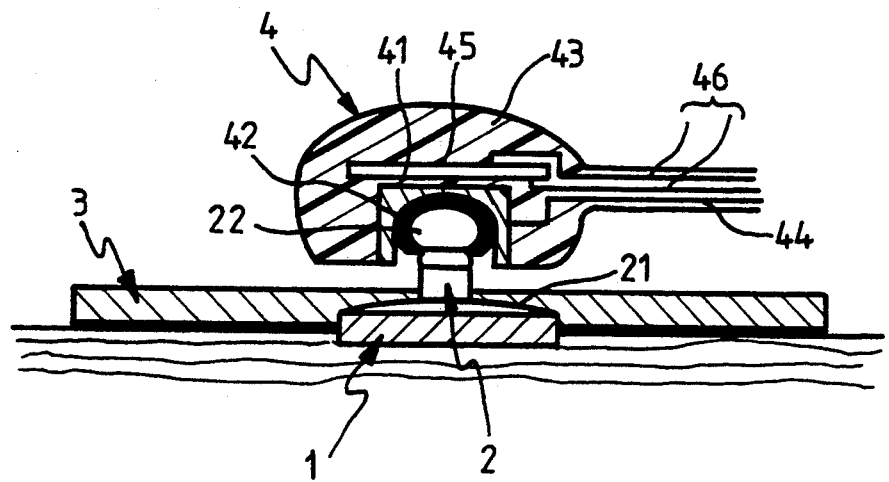

ELECTRODE CONNECTOR, IN PARTICULAR FOR ELECTROCARDIOGRAM ELECTRODES, AND ELECTRODE ASSEMBLY COMPRISING A CONNECTOR OF THIS KIND

BACKGROUND OF THE INVENTION

1. Field of the Invention

The invention concerns an electrode connector, in particular a connector for electrodes for non-invasive recording of vital signs and therefore adapted to be applied to the skin of a patient, for example an electrocardiogram electrode comprising a foam material pad impregnated with a gel which is a good conductor of electricity and a peg also made from a material that is a good conductor in contact with the pad and having a connection head. The invention also concerns an electrode assembly comprising an electrode of this kind and a connector of this kind.

2. Description of the Prior Art

During non-invasive recording of vital signs continuously over a complete day of normal activity of the patient, who is therefore moving around, an electrode of this type is used which further comprises a flexible material disk able to deform locally to the shape of the body of the patient, one side of which is coated with an adhesive so that it can be stuck to the skin of the patient and which has a central hole so that it can be threaded over the electrode head and attached to the impregnated foam pad.

To record the signals, for example the signals constituting an electrocardiogram, several similar electrodes are placed at appropriate locations on the body, for example on the chest, of the patient in order to record the potential difference between two particular electrodes, taking one electrode as a reference potential.

FIG. 1 shows an electrode of this kind. The figure shows the foam pad 1 impregnated with an electrically conductive gel adapted to be applied to the skin of a patient. The side of it that is in contact with the skin of the patient is in contact with a base portion of the peg 2. The disk 3 with a central hole so that it can be threaded over the peg 1 and whose inner surface is coated with an adhesive for fixing the electrode to the skin of the patient is also made from a foam material.

At the end opposite its base portion 21 in contact with the pad 1 the peg 2 comprises an enlarged head 22 to which a connector 4 may be attached snap-fastener fashion.

The head 22 and the connector 4 are usually constructed in a similar way to a "popper" as used on garments.

To this end the connector 4 comprises an electrically conductive material contact member 41 adapted to bear against the head 22 of the electrode where it is held by a snap-fastener member 22 such as a split spring washer or a spring clip with two branches or any like device accommodated in the contact member 41. This assembly is in turn accommodated inside an electrically insulative material protective cap 43. A single-conductor electrical cable 44 connects the contact member 41 to a terminal of a recording device, in this example an electrocardiograph (not shown). The cap 43 may incorporate a metal shield connected by a ground braid integrated in the electrical cable to a ground terminal of the recording device to prevent the signal picked up by the electrode being degraded by radiated interference.

However, it is important that while the patient is wearing the electrodes the conductors connected to them are not subject to any unwanted movements which apply traction to the electrodes. Likewise it is important that the electrodes themselves are not subjected to impact or other forces such as may be caused by accidental rubbing. Experience has shown that even though precautions may be taken, it is not always possible to avoid these momentary loads on the wires and/or the electrodes themselves.

These stresses, impacts, rubbing, etc generate spurious voltages which constitute artefacts which are also recorded on the electrocardiogram and which make the latter difficult to read and interpret.

A conventional way to prevent such artefacts occurring is simply to immobilize the conductors connected to the electrodes by fixing them to the skin of the patient at some distance from the electrode using pieces of adhesive tape and forming a loop in the conductor so that there is some slack between the adhesive tape and the connector. This is uncomfortable for the patient, however, and not entirely effective as it does not avoid the problems associated with forces exerted directly on the electrode or the connector.

Known cup-shape electrode protector devices designed to fit over the electrode comprise a peripheral ring covered with an adhesive that is stuck onto the skin of the patient after immobilizing the conductor wire(s) between the adhesive side of the ring and the skin, once again forming a loop.

This method is more effective but still has drawbacks in that it requires some skill on the part of the personnel who fit the equipment to the patient, it means that fitting takes longer, it increases the overall size of the electrode and detaching it when the electrode is to be removed may cause the patient some discomfort.

An object of the invention is to remedy these drawbacks.

SUMMARY OF THE INVENTION

In one aspect, the present invention consists in an electrode connector suitable for electrocardiogram electrodes having a connection head made from a material that is a good conductor of electricity, the connector comprising a contact member made from a material that is a good conductor of electricity and that is adapted to contact said connection head, a member for snap-fastening said connector to said connection head, an electrically insulative material protective cap at least partially enclosing said contact member, an electric cable comprising at least one electric conductor connected to said contact member and a device for detecting strain generating artefacts and comprising a strain sensor accommodated in said cap between at least part of said contact member and at least one interior area of said cap and at least one other electric conductor connected to said strain sensor.

In another aspect, the present invention consists in an electrode assembly, for example an electrocardiogram electrode assembly, comprising an electrode having a connection head connected electrically to a pad impregnated with an electrically conductive gel and a connector comprising a contact member made from a material which is a good conductor of electricity and adapted to contact said connection head, a member for snap fastening said connector to said connection head, an electrically insulative material protective cap at least partially enclosing said contact member and an electric cable comprising at least one electric conductor connected to said contact member, in which electrode assembly said connector further comprises a device for detecting strain generating artefacts and comprising a strain sensor accommodated in said cap between at least part of said contact member and at least one interior area of said cap and at least one other electric conductor connected to said strain sensor.

Other features and advantages of the invention will emerge from the following description given by way of non-limiting example with reference to the appended drawings.

BRIEF DESCRIPTION OF THE DRAWINGS

FIG. 1 is a diagrammatic view in cross-section of a conventional electrode assembly.

FIG. 2 is a diagrammatic view in cross-section of an electrode assembly according to the invention.

DETAILED DESCRIPTION OF THE INVENTION

Like that shown in FIG. 1, the electrode assembly shown in FIG. 2 comprises an electrocardiogram electrode and a connector, the electrode comprising a foam material pad 1 impregnated with a gel which is a good conductor of electricity adapted to be applied to the skin of a patient and a peg 2 which is also made from a material which is a good conductor of electricity, for example of metal, having a base portion 21 in contact with the side of the pad 1 opposite that in contact with the skin of the patient. The peg also has a connection head 22 with an enlarged free end so that the connector may be attached snap-fastener fashion. A flexible material disk 3 is fastened to the pad 1 and is able to deform to the shape of the body of the patient. One side of it is coated with an adhesive so that it can be stuck to the skin of the patient and it has a central hole so that it can be fitted over the connection head and fastened to the impregnated foam pad. This disk may also be made from foam.

The connector 4 includes a contact member 41 made from a material that is a good conductor of electricity, for example of metal, adapted to bear against the connecting head 22 of the electrode and at least partially accommodated within an electrically insulative material protective cap 43, a removable snap-fastener member 42 accommodated in the contact member 41 to hold the latter in contact with the connecting head 22 in the snap-fastened position and an electrically insulative material protective cap 43 within which the contact member is at least partially accommodated. The snap-fastener member 42 is, for example and in a manner that is known in itself, a split spring washer or a spring clip with two branches. An electric cable comprises a conductor 44 connecting the contact member 41 to an input terminal of an electrocardiograph (not shown).

In accordance with the invention, the connector is additionally provided with a device for detecting strain which generates artefacts. This device comprises a strain sensor 45 disposed between at least part of the contact member 41 and the back of the protective cap 43 plus electrical conductors 46 connected to the strain sensor 45 to transmit any signal it produces to a system adapted to subtract this signal from the signal corrupted by the artefacts obtained from the pad 1 via the peg 2, the contact member 41 and the conductor 44.

The strain sensor 45 may advantageously comprise a plate with two parallel plane surfaces one of which is near or is in contact with a corresponding plane surface of the contact member 41.

In one specific embodiment of the invention this plate carries an element responsive to mechanical strain, for example a resistive type strain gauge.

In another specific embodiment of the invention the plate itself is responsive to strain, being made from a piezo-electric material such as a piezo-electric ceramic material.

The two electric conductors 46 connected either to respective terminals of the sensitive element integrated into the plate or carried by it or to the respective two sides of the latter if it in itself constitutes the sensitive element are preferably two conductors of the electric cable of which one conductor 44 is connected to the contact member 41 to transmit the signal from the pad 1. In some cases a single conductor 46 may suffice, the strain signal being transmitted by the conductor 46 connected to the sensor 45 and the conductor 44 connected to the contact member 41.

With this arrangement any mechanical strain on the electric cable or on the connector 4 and transmitted to the electrode itself to generate artefacts also generates a voltage across the sensor and this voltage is transmitted by the conductors 46 to the subtractor system which may, for example, be part of the equipment for recording the electrocardiogram voltage. This equipment is therefore able to display an electrocardiogram voltage which is free of artefacts by virtue of the subtraction of the signal appearing across the sensor 45 from the voltage transmitted to the equipment by the conductor 44 connected to the electrode head or by virtue of some other electronic processing. The cap 43 may incorporate a metal shield connected to a grounding terminal by a braided sheath around the conductors 44, 46. Assuming that subtraction cannot provide a result that is regarded as acceptable, it is also feasible to have the signal from the sensor disable the signal processing or analysis currently in progress. Management of the use of the signal from the sensor is advantageously implemented by means of a microprocessor-based circuit.

The invention is naturally not limited to the embodiments as shown and described hereinabove and other embodiments may be put forward without departing from the scope of the invention. For example, the invention may be implemented in respect of electrodes other than electrocardiogram electrodes.

There is claimed:

1. Electrode connector suitable for electrocardiogram electrodes having a connection head made from a material that is a good conductor of electricity, the connector comprising a contact member made from a material that is a good conductor of electricity and that is adapted to contact said connection head, means for snap-fastening said connector to said connection head, an electrically insulative material protective cap at least partially enclosing said contact member, an electric cable comprising at least one electric conductor connected to said contact member and a device for detecting strain generating artefacts and comprising a strain sensor accommodated in said cap between at least part of said contact member and at least one interior area of said cap and at least one other electric conductor connected to said strain sensor.

2. Connector according to claim 1 wherein said strain detecting device comprises a strain sensor in the form of a plate carrying an element responsive to strain.

3. Connector according to claim 1 wherein said strain detecting device comprises a strain sensor in the form of a plate which is responsive to strain.

4. Connector according to claim 1 wherein said sensor is made from a piezo-electric material.

5. Connector according to claim 1 wherein said sensor is made from a piezo-electric ceramic material.

6. Connector according to claim 1 wherein said sensor carries a resistive strain gauge.

7. Connector according to claim 1 further comprising two electric conductors connected to said strain sensor.

8. Connector according to claim 1 further comprising said at least one other electric conductor connected to said strain sensor associated with said at least one electric conductor connected to said contact member constituting said electric cable.

9. An electrode assembly comprising an electrode having a connection head; a pad impregnated with an electrically conductive gel connected to said electrode; and a connector comprising a contact member made from a material which is a good conductor of electricity and adapted to contact said connection head, means for snap fastening said connector to said connection head, an electrically insulative material protective cap at least partially enclosing said contact member and an electric cable comprising at least one electric conductor connected to said contact member, said connector further comprising a device for detecting strain generating artefacts and comprising a strain sensor accommodated in said cap between at least part of said contact member and at least one interior area of said cap and at least one other electric conductor connected to said strain sensor.

* * * * *